US010328244B2

(12) United States Patent
Eliasen et al.

(10) Patent No.: US 10,328,244 B2
(45) Date of Patent: Jun. 25, 2019

(54) PERIPHERAL ANTEGRADE PERFUSION AND OCCLUSION DEVICE

(71) Applicant: EDWARDS LIFESCIENCES CORPORATION, Irvine, CA (US)

(72) Inventors: Kenneth Eliasen, Cottonwood Heights, UT (US); Adam J. Yestrepsky, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 475 days.

(21) Appl. No.: 14/907,241

(22) PCT Filed: Jun. 24, 2015

(86) PCT No.: PCT/US2015/037513
§ 371 (c)(1),
(2) Date: Jan. 22, 2016

(87) PCT Pub. No.: WO2015/200532
PCT Pub. Date: Dec. 30, 2015

(65) Prior Publication Data
US 2016/0158506 A1  Jun. 9, 2016

Related U.S. Application Data

(60) Provisional application No. 62/016,422, filed on Jun. 24, 2014.

(51) Int. Cl.
*A61B 17/12* (2006.01)
*A61M 25/10* (2013.01)
*A61M 39/22* (2006.01)

(52) U.S. Cl.
CPC ....... *A61M 25/10* (2013.01); *A61B 17/12036* (2013.01); *A61B 17/12109* (2013.01);
(Continued)

(58) Field of Classification Search
CPC .......... A61M 39/22; A61M 25/10; A61M 2025/105; A61M 2025/1081;
(Continued)

(56) References Cited

U.S. PATENT DOCUMENTS 5,161,428 A    11/1992  Petruccello
5,333,614 A *   8/1994  Feiring ............... A61B 8/06
                                              600/456
(Continued)

FOREIGN PATENT DOCUMENTS

WO    2013118807 A1    8/2013

*Primary Examiner* — Theodore J Stigell
(74) *Attorney, Agent, or Firm* — Klarquist Sparkman, LLC

(57) ABSTRACT

This disclosure relates generally to systems and methods for occluding vessels of the heart and inducing cardioplegic arrest to facilitate the performance of cardiac procedures. An aortic occlusion and perfusion device includes an expandable member configured to expand within the aorta to secure the device within the aorta, and a catheter extending proximally from the expandable member and in fluid communication with the expandable member. The catheter can define a plurality of openings along its length through which blood can pass with one or more of the openings located proximal to the expandable member and one or more of the openings located within the expandable member. The device can also include a flow control sheath disposed around the catheter member such that axial movement of the flow control sheath relative to the catheter selectively occludes or uncovers one or more of the openings located proximal to the expandable member.

17 Claims, 3 Drawing Sheets

(52) U.S. Cl.
CPC ....... *A61B 17/12136* (2013.01); *A61M 39/22* (2013.01); *A61B 17/1204* (2013.01); *A61M 2025/105* (2013.01); *A61M 2025/1052* (2013.01); *A61M 2025/1079* (2013.01); *A61M 2025/1081* (2013.01); *A61M 2025/1097* (2013.01)

(58) Field of Classification Search
CPC .. A61M 2025/1052; A61M 2025/1079; A61M 2025/1097; A61B 17/12036; A61B 17/12109; A61B 17/12136; A61B 17/1204
See application file for complete search history.

(56) References Cited

U.S. PATENT DOCUMENTS

| | | | |
|---|---|---|---|
| 5,394,770 | A | 3/1995 | Boike et al. |
| 6,547,760 | B1 * | 4/2003 | Samson ........... A61B 17/12045 604/101.01 |
| 6,908,454 | B2 | 6/2005 | McFarlane |
| 7,175,184 | B1 | 2/2007 | Rinner et al. |
| 7,316,669 | B2 | 1/2008 | Ranalletta |
| 9,149,606 | B2 | 10/2015 | Beissel et al. |
| 9,326,784 | B2 | 5/2016 | Ravikumar |
| 9,636,105 | B2 | 5/2017 | Bagaoisan et al. |
| 2010/0222637 | A1 * | 9/2010 | Kassab .............. A61B 5/02152 600/17 |
| 2013/0184742 | A1 | 7/2013 | Ganesan et al. |
| 2014/0336584 | A1 | 11/2014 | McFarlane |
| 2015/0051584 | A1 | 2/2015 | Korkuch et al. |
| 2015/0123355 | A1 | 5/2015 | Castro et al. |
| 2015/0148747 | A1 | 5/2015 | Whitley |

* cited by examiner

PERIPHERAL ANTEGRADE PERFUSION AND OCCLUSION DEVICE

FIELD

This disclosure relates generally to devices and techniques for performing cardiac procedures and particularly to catheter systems and methods for occluding vessels and introducing blood into vessels.

BACKGROUND

Techniques for performing major surgeries such as coronary artery bypass grafting and heart valve repair and replacement generally require open access to the thoracic cavity through a large open wound, known as a thoracotomy. Typically, the sternum is cut longitudinally (i.e., a median sternotomy), providing access between opposing halves of the anterior portion of the rib cage to the heart and other thoracic vessels and organs. An alternate method of entering the chest is via a lateral thoracotomy, in which an incision, typically 10 cm to 20 cm in length, is made between two ribs. A portion of one or more ribs may be permanently removed to optimize access.

In procedures requiring a median sternotomy or other type of thoracotomy, the ascending aorta is readily accessible for placement of an external cross-clamp, and for introduction of a cardioplegic fluid delivery cannula and venting cannula through the aortic wall. However, such surgery often entails weeks of hospitalization and months of recuperation time, in addition to the pain and trauma suffered by the patient. Moreover, while the average mortality rate associated with this type of procedure can be significant for first-time surgery, mortality and morbidity can be significantly increased for reoperation. Further, significant complications may result from such procedures. For example, application of an external cross-clamp to a calcified or atheromatous aorta may cause the release of emboli into the brachiocephalic, carotid or subclavian arteries with serious consequences such as strokes.

Methods and devices have therefore been developed for isolating the heart and coronary arteries from the remainder of the arterial system, arresting cardiac function, and establishing cardiopulmonary bypass without the open-chest access provided by a median sternotomy or other type of thoracotomy. In particular, methods and devices have been developed which facilitate the delivery of cardioplegia sufficiently to allow the heart to be placed under cardioplegic arrest with full cardiopulmonary bypass, without requiring open-chest access to the heart and without requiring an incision or puncture in the aorta, in the pulmonary artery, or in the heart wall. However, many such devices require separate lumens or entirely separate catheters for perfusion blood and fluids used to expand or inflate occlusion members. Accordingly, improvements to aortic occlusion and perfusion devices are desirable.

SUMMARY

Disclosed embodiments of the present application provide aortic occlusion and perfusion devices and methods that address certain deficiencies of known occlusion devices and methods. In one representative embodiment, an aortic occlusion and perfusion device comprises an expandable member configured to expand within the aorta to secure the device within the aorta, and a catheter extending proximally from the expandable member and in fluid communication with the expandable member. The catheter can define a plurality of openings along its length through which blood can pass with one or more of the openings located proximal to the expandable member and one or more of the openings located within the expandable member. The device can also include a flow control sheath disposed around the catheter proximal to the expandable member such that axial movement of the flow control sheath relative to the catheter selectively occludes or uncovers one or more of the openings located proximal to the expandable member.

In another representative embodiment, a method of occluding blood flow through the aorta comprises inserting an aortic occlusion device including an expandable member into a patient's vasculature, positioning the aortic occlusion device in the aortic arch such that a distal end portion of the expandable member is located adjacent the ascending aorta and a proximal end portion of the expandable member is located adjacent the descending aorta, and expanding the expandable member with blood supplied by a catheter in fluid communication with the expandable member. The method can further include controlling the pressure inside the expandable member by varying the flow rate of blood exiting the catheter through one or more openings defined in the catheter proximal to the expandable member.

The foregoing and other objects, features, and advantages will become more apparent from the following detailed description, which proceeds with reference to the accompanying figures.

DETAILED DESCRIPTION

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to a surgical access site (i.e., away from the heart). As used herein, the term "distal" refers to a position, direction, or portion of a device that is further away from a surgical access site (i.e., closer to the heart). Thus, for example, proximal motion of a device is motion of the device toward the surgical access site, while distal motion of the device is motion of the device toward the heart. The terms "longitudinal" and "axial" refer to an axis extending in the proximal and distal directions, unless otherwise expressly defined.

Figure 1:
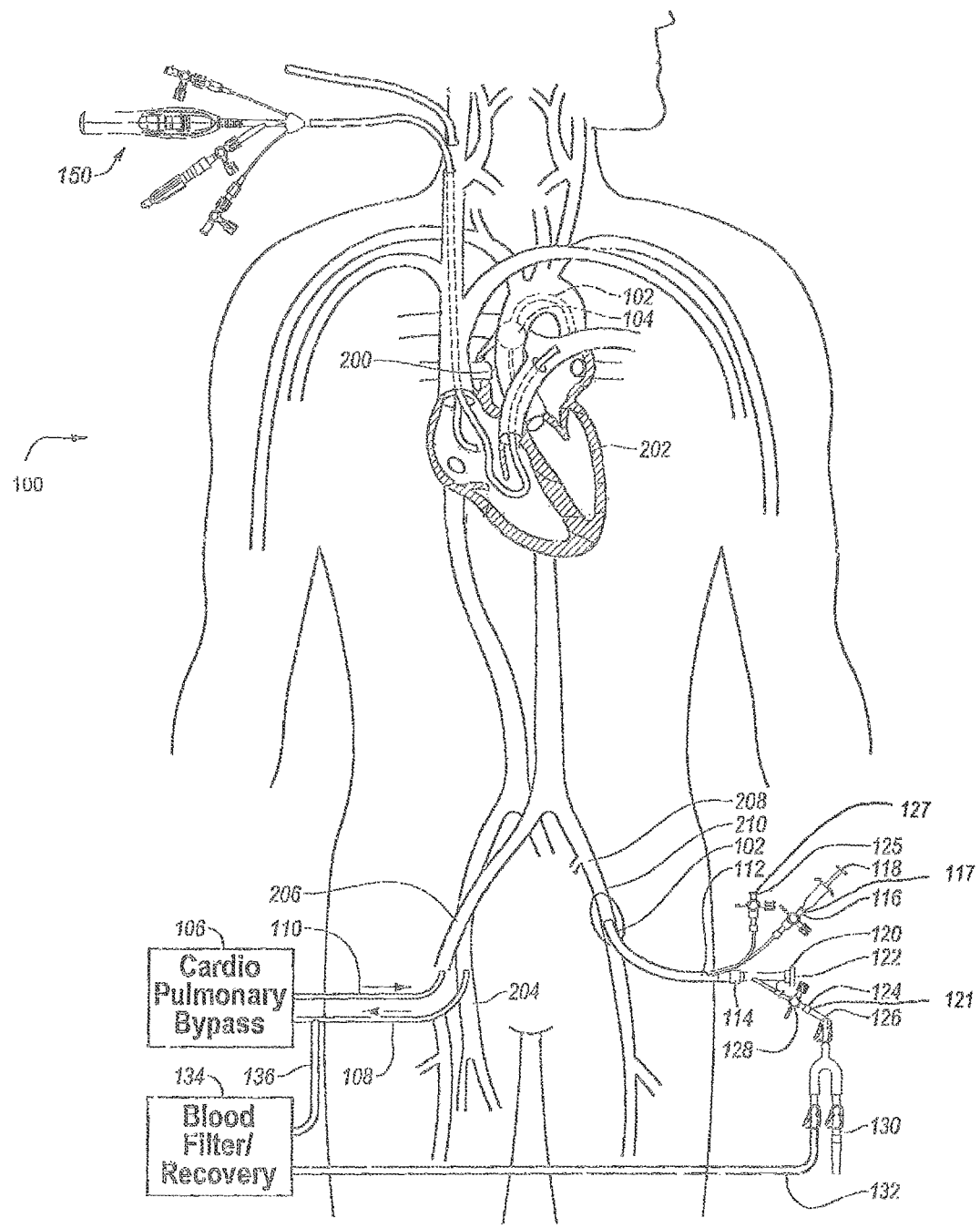
FIG. 1 is a schematic illustration of a representative cardiac access system.

FIG. 1 schematically illustrates an exemplary cardiac access system 100 and various individual components thereof. The cardiac access system 100 may also be referred to as a cardiac occlusion system as, in some embodiments, the cardiac access system 100 may occlude the aorta, coronary sinus, and/or other cardiac vasculature or lumens. The cardiac access system 100 illustrated in FIG. 1 is intended to provide a general overview of one example of a suitable system for accessing a patient's heart or a portion thereof, and is not intended to be an exhaustive illustration of all components or mechanisms that may be in use during a cardiac procedure.

The cardiac access system 100 can include a first delivery catheter 102. In this embodiment, the first delivery catheter 102 is elongated and is used to access the aorta, although the first delivery catheter 102 may optionally be used to occlude or access other lumens within the body. In the illustrated embodiment, a representative expandable member 104 is located at a distal portion of the delivery catheter 102. When the expandable member 104 is inflated or otherwise expanded, such as is illustrated in FIG. 1, the expandable member 104 may occlude the ascending aorta 200, thereby separating the left ventricle 202 and the upstream portion of the ascending aorta 200 from the rest of the patient's arterial system. Expansion of the expandable member 104 may also be used to securely position the distal end of the delivery catheter 102 within the ascending aorta 200, as the exterior of the expandable member 104 may expand to engage the interior surface of the ascending aorta 200.

In the embodiment of FIG. 1, a cardiopulmonary bypass system 106 may be used to remove venous blood from the body by, for instance, being placed in fluid communication with the femoral vein 204. A blood withdrawal catheter 108 may connect to the femoral vein 204 and the cardiopulmonary bypass system 106 and be used to remove blood so as to allow the cardiopulmonary bypass system 106 to remove carbon dioxide from the blood, oxygenate the blood, and then return the oxygenated blood to the patient. The oxygenated blood may be returned through a return catheter 110 that accesses the femoral artery 206. The oxygenated blood may be returned at sufficient pressure so as to flow throughout the patient's arterial system except for the portion blocked by the expanded occluding member 104 on the aortic occluding catheter 102.

The first delivery catheter 102 of the illustrated embodiment extends through the descending aorta to the left femoral artery 208 and out of the patient through an access site 210, which may be formed as a cut down or in any other suitable manner. A proximal section 112 of the catheter 102 may extend out of the patient through the access site 210. In this embodiment, an adapter 114 may connect to the proximal section 112 of the catheter 102. The adapter 114 is illustrated as having four arms, although a suitable adapter may have more or less than four arms. In one embodiment, a first arm 116 with a first access port 117 may be adapted for use with the expandable member 104. For instance, an inflation device 118 may be used to inject air or some other fluid that can inflate the expandable member 104. In some embodiments, the inflation fluid can be oxygenated blood supplied by the cardiopulmonary bypass system 106. A second arm 120 optionally includes a main access port 122 through which instrumentation or other materials or components may pass. For instance, endovascular devices, valve prostheses, angioscopes, irrigation or cardioplegic fluids, or other components or materials, or any combination of the foregoing, may pass through the main access port 122, through the catheter 102, and out of a distal port of the catheter 102. In one example embodiment, the main access port 122 is coupled to a source of cardioplegic fluid (not shown) which is delivered through the catheter 102 to arrest the patient's heart.

The adapter 114 of FIG. 1 can also include a third arm 124 with a third access port 121 connected to a by-pass line 126 that is provided to direct blood, irrigation fluid, cardioplegia solution, and the like to or from the system. A suitable valve 128 may also be provided to open and close the by-pass line 126 and/or direct fluid passing through the by-pass line to a discharge line 130 or a line 132 to a blood filter and recovery unit 134. A return line 136 may be provided to return any filtered blood to the cardiopulmonary by-pass system 106. The adapter 114 can also include a fourth arm 125. The fourth arm 125 with fourth access port 127 may, in some embodiments, be in fluid communication with the aortic root (e.g., through a pressure port in the distal end of the catheter 102) and/or a pressure monitoring device (not shown) proximate the adapter 114. Thus, the fourth arm 125 may facilitate measuring of the root pressure within the patient's aorta.

Still referring to FIG. 1, an exemplary set-up of the cardiac access system 100 will be described in additional detail. More particularly, to set up the cardiac access system 100, the patient may initially be placed under light general anesthesia. The withdrawal catheter 108 and the return catheter 110 of the cardiopulmonary by-pass system 106 can be percutaneously introduced into the right femoral vein 154 and the right femoral artery 156, respectively. An incision 210 may be made in the left groin to expose the left femoral artery 208, and the aortic occluding catheter 102 is inserted into the left femoral artery 208 through the incision 210 and advanced upstream until the expandable member 104 of the occluding catheter 102 is within the ascending aorta 200. Antegrade cardioplegic fluid may then pass through the occluding catheter 102 and into the aorta. In one embodiment, an initial volume of about 1000-1500 ml of cardioplegic fluid is delivered through the interior inner lumen 140 of the aortic occlusion catheter 102, and such delivery may initiate cardioplegic arrest, after which cardioplegic arrest may be maintained by retrograde delivery through the delivery catheter 150.

The operation of the cardiopulmonary by-pass unit 106 can be initiated to withdraw blood from the femoral vein 204 through the catheter 108, remove $CO_2$ from the withdrawn blood, add oxygen to the withdrawn blood, and then pump the oxygenated blood through the return catheter 110 to the right femoral artery 206. The expandable member 104 may then be inflated or otherwise expanded to occlude the ascending aorta 200, causing the blood pumped out of the left ventricle to flow through a discharge port 123 into the first interior lumen 140 of the occluding catheter 102. The blood may flow through the interior lumen 140 and out the third arm 124 of the adapter 114 into the by-pass line 126 and then into a blood filter and recovery unit 134 through the valve 128 and line 132. For blood and irrigation fluids containing debris and the like, the position of the valve 128 may be changed to direct the fluid through the discharge line 130.

With the cardiopulmonary by-pass system in operation, the heart may become completely paralyzed and stop pumping. The left atrium may become decompressed and the ascending aorta can be blocked by the expandable member 104 on the occluding catheter 102. At such point in time, the heart may be appropriately prepared for a cardiac procedure. The procedures with which the system and method of the present disclosure are useful include thoracoscopic coronary artery bypass grafting, thoracoscopic or endovascular repair or replacement of the mitral, aortic and other valves, thoracoscopic repair of atrial or ventricular septal defects and other congenital defects, transmyocardial laser revascularization, electrophysiological mapping and ablation, and various other procedures which require or would benefit from the inducement of cardioplegic arrest. The present disclosure may also be utilized to induce cardioplegic arrest in conventional open surgical procedures as a substitute for conventional external aortic cross-clamps and conventional cardioplegia cannulae introduced directly into the heart and/or aorta.

Figure 2:
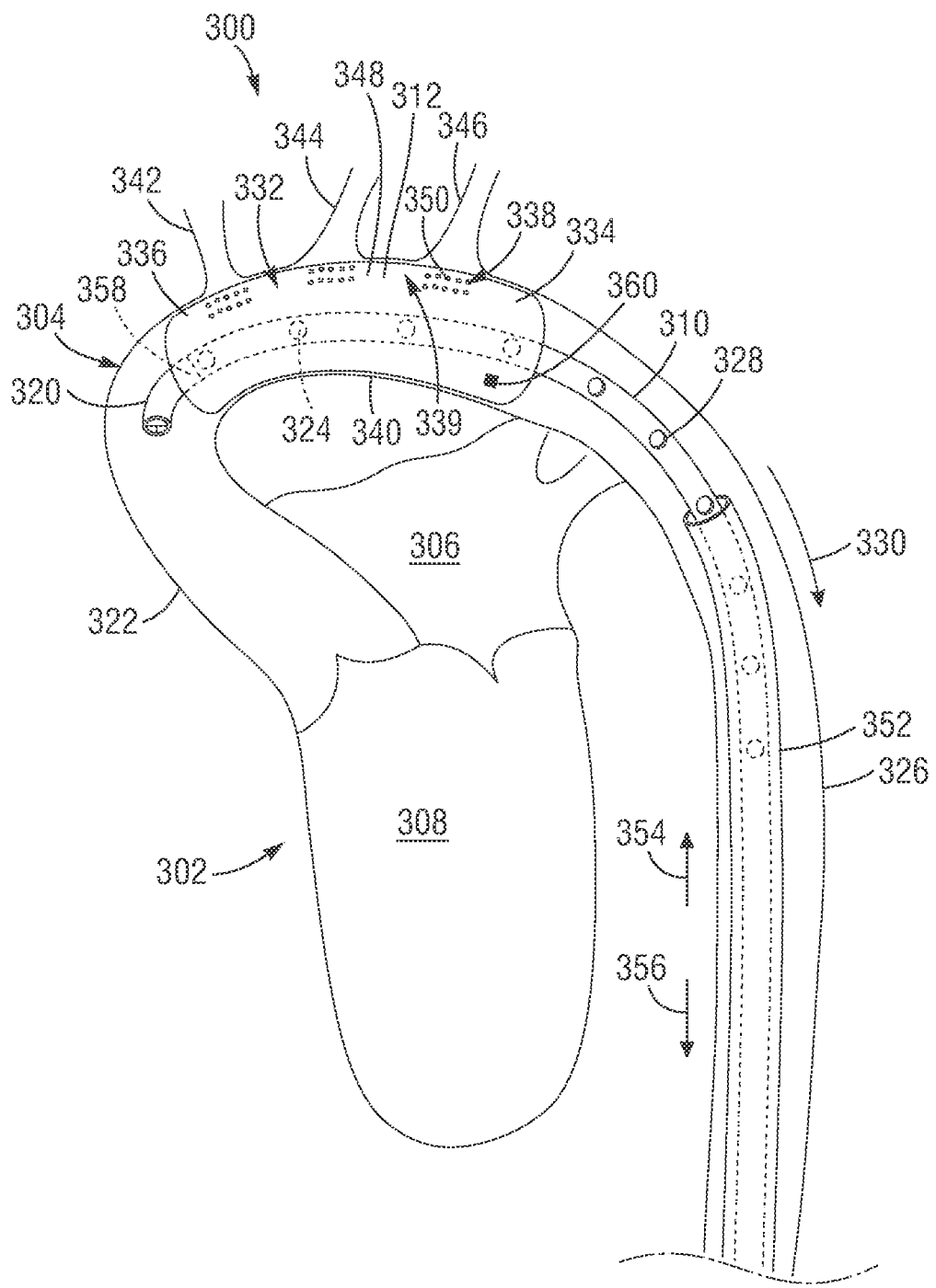
FIG. 2 schematically illustrates an aortic occlusion device located in the aortic arch.

FIG. 2 illustrates an exemplary embodiment of an aortic occlusion and perfusion device 300, such as may be used in combination with the cardiac access system described above. For purposes of illustration, the device 300 is shown located in a partial cross-section of a human heart 302 including only the aorta 304, the left atrium 306, and the left ventricle 308. The device 300 can include a catheter 310 in fluid communication with an expandable member 312 in the form of an inflatable balloon, and can be inserted into a patient's vasculature and located at a desired location, such as within the aorta 304 of the patient. Accordingly, the catheter 310 may have a length such that when the expandable member 312 is located in the aorta 304, a proximal end (not shown) of the catheter 302 may remain outside the patient and accessible to a surgeon, such as through the access ports of the system of FIG. 1.

Figure 3:
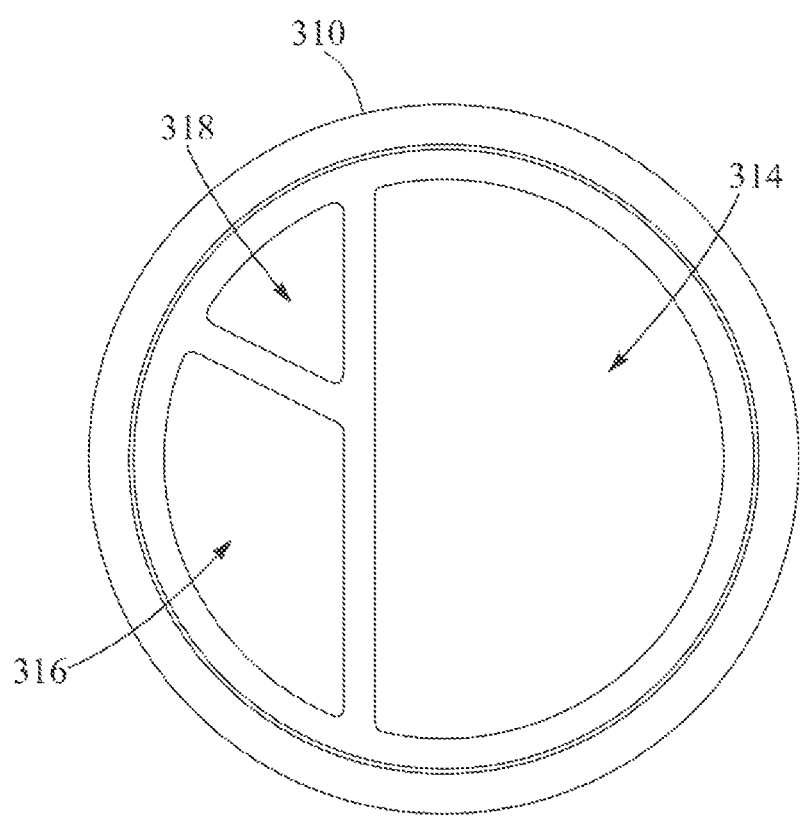
FIG. 3 is a cross-sectional view of a representative embodiment of a catheter.

As shown in FIG. 3, the catheter 310 can define one or more interior lumens, such as first, second, and third lumens 314, 316, 318. The lumens 314, 316, 318 can be useful for, for example, delivery and removal of instruments, introducing cardioplegic fluid into the heart, conducting blood or other materials into or out of the body, conducting signals indicative of fluid pressure, temperature, or other parameters, and/or other uses. In the embodiment shown, the first lumen 314 can comprise greater than 50% of the cross-sectional area of the catheter 310. However, in alternative embodiments, the catheter 310 can define any suitable number of interior lumens having any suitable cross-sectional area. In some embodiments, the catheter 310 can extend through the interior of the expandable member 312, as shown in FIG. 2. In other embodiments, the catheter 310 can extend through any suitable portion of the interior of the expandable member 312, or can terminate at a proximal end of the expandable member 312, as desired.

In the embodiment shown, a proximal end portion of the first lumen 314 can be in fluid communication with a single outlet of a cardiopulmonary bypass machine, or other extracorporeal source, and can be configured to direct a flow of oxygenated blood along the length of the catheter 310. In this manner, a single lumen (i.e., first lumen 314) in fluid communication with a single blood source can supply blood flow to both the expandable member 312 and a lower portion of a patient's body, as further described below. A distal end portion of the first lumen 314 can be in fluid communication with the interior of the expandable member 312 via one or more inflation ports 324 defined by the catheter 310. The one or more inflation ports 324 can allow blood to flow out of the first lumen 314 into the expandable member 312, thereby expanding or inflating the expandable member 312. In the embodiment shown, the catheter 310 includes four inflation ports 324 equally spaced along the catheter 310 within the expandable member 312. However, in alternative embodiments, the catheter 310 can include any suitable number of inflation ports having any suitable spacing, including a single inflation port.

The first lumen 314 can also be in fluid communication with the descending aorta 326 via a plurality of perfusion ports 328 defined in the catheter 310. The plurality of perfusion ports 328 can be located on the catheter 310 proximally of the expandable member 312, and can allow oxygenated blood to flow out of the first lumen 314 into the descending aorta 326. The blood can then flow along the descending aorta 326 in the antegrade direction, as indicated by arrow 330, to perfuse a lower portion of the patient's body. In the embodiment shown, the catheter 310 includes six perfusion ports 328 equally spaced along the catheter 310. However, in alternative embodiments, the catheter 310 can include any suitable number of perfusion ports having any suitable spacing.

The expandable member 312 can comprise a generally tubular body 332 having a proximal end portion 334 and a distal end portion 336, and can be expandable or inflatable so as to occlude the aorta 304 or other vessel of the heart 302. In the embodiment shown, the expandable member 312 can be configured to be located in the aortic arch 340 substantially adjacent the brachiocephalic artery 342, the left common carotid artery 344, and the left subclavian artery 346, collectively referred to as the head vessels. In some embodiments, the distal end portion 336 can be configured to expand to a greater size or diameter than the proximal end portion 334 to, for example, provide for greater sealing capability between the distal end portion 336 and the tissue of the aorta 304. This can reduce leakage of perfusion blood past the distal end portion 336, and can reduce retrograde migration of the expandable member 312 along the aortic arch 340 due to the pressure of perfusion blood in the descending aorta 326.

The expandable member 312 can include one or more porous regions such as representative porous region 338 located on an upper portion 348 of the expandable member 312. In the embodiment shown, the expandable member 312 can include three distinct porous regions such as porous region 338 axially spaced apart axially from one another by non-porous regions, such as non-porous region 339. Each respective porous region 338 can be located adjacent one of the head vessels 342, 344, 346, as shown in FIG. 2.

In the embodiment shown, the one or more porous regions such as representative porous region 338 can comprise a plurality of openings such as representative opening 350 defined in the upper portion 348 of the expandable member 312. The plurality of openings such as opening 350 can be in fluid communication with the interior of the expandable member 312. In this manner, the one or more porous regions such as representative porous region 338 can allow blood to flow out of the expandable member 312 through the openings such as opening 350 to perfuse the head vessels 342, 344, 346. Additionally, this configuration allows blood directed toward the head vessels 342, 344, 346 to flow in the retrograde direction from the cardiopulmonary bypass system, or other source, to the expandable member 312 entirely within the first lumen 314 of the catheter 310, rather than flowing freely through the descending aorta 326 (and optionally through additional arteries such as the femoral artery, depending upon the access site). This can reduce the risk of emboli formation by limiting the amount of retrograde blood flow in the arteries attendant to cardiopulmonary bypass, thereby reducing the risk of embolism.

In some embodiments, the one or more porous regions such as representative porous region 338 can extend around the circumference of the expandable member 312. This can reduce the complexity of positioning the expandable member 312 in the aortic arch by allowing the expandable member 312 to be longitudinally positioned beneath the head vessels 342, 344, 346 in any rotational orientation. In some embodiments, the one or more porous regions such as porous region 338 can have a uniform width, or can have different widths. In some embodiments, the one or more porous regions such as porous region 338 can include a plurality of openings such as representative opening 350 having a uniform size and arranged in a grid-like pattern. Alternatively, the openings such as opening 350 can have different sizes, and can be arranged in any suitable pattern, or at random. In some embodiments, the one or more porous regions such as porous region 338 can extend around less than the entire circumference of the expandable member 312, such as halfway around the circumference, as desired.

In some embodiments, the one or more porous regions such as representative porous region 338 can comprise a single porous region that can be adjacent to and in fluid communication with all of the head vessels 342, 344, 346. This can reduce the complexity of longitudinally positioning the expandable member 312 by eliminating the need to position the expandable member 312 such that individual porous regions are located adjacent their respective vessels. This can also allow the device 300 to accommodate variation in the location of the head vessels 342, 344, 346 from patient to patient. In some embodiments, the single porous region can extend from the proximal end to the distal end of the expandable member 312. However, in alternative embodiments, the single porous region can terminate at any suitable distance distal of the proximal end and/or proximal of the distal end of the expandable member 312. In some embodiments, the single porous region can include a plurality of openings such as representative opening 350, which can have a uniform or non-uniform size, and can be arranged in any suitable pattern or at random, as described above.

In some embodiments, the plurality of openings such as representative opening 350 can comprise valves or slits in the expandable member 312 configured to open or crack when the pressure inside the expandable member 312 reaches a predetermined pressure. In this manner, the plurality of openings such as opening 350 can be configured to perfuse the head vessels 342, 344, 346 when, for example, the expandable member 312 has expanded sufficiently to occlude the aorta 304. In some embodiments, each of the one or more porous regions 338 can comprise a single valve or a single slit corresponding to a respective head vessel and configured to open when the pressure within the expandable member 312 reaches a predetermined pressure. In some embodiments, the plurality of openings such as representative opening 350 can be configured to vary in size as the expandable member 312 expands and/or contracts. For example, the plurality of openings such as representative opening 350 can be configured to increase in size as the expandable member 312 expands, and to decrease in size as the expandable member 312 contracts. In this manner, the blood flow out of the expandable member 312 can be increased as the expandable member 312 increases in size, and decreased as the expandable member 312 decreases is size.

In some embodiments, the one or more porous regions such as porous region 338 can comprise a single continuous slit extending along the upper portion 348 of the expandable member 312 adjacent all of the head vessels 342, 344, 346. For example, the single slit can overlap the ostium of each of the head vessels 342, 344, 346 such that the slit can perfuse all of the head vessels at once.

In some embodiments, one or more of the inflation ports 324 and/or one or more of the perfusion ports 328 can comprise valves or slits, which can be configured to open when the pressure within the first lumen 314 reaches a predetermined pressure.

In some embodiments, the expandable member 312 can include one or more porous members, such as one or more mesh materials or membranes, such as for allowing blood flow while also providing elastic structure to the expandable member 312, and/or for capturing embolic material entrained in the blood flow without unduly disrupting blood flow out of the expandable member 312 into the head vessels. For example, in some embodiments the expandable member 312 can include a filter mesh disposed on the exterior of the catheter 310 inside the expandable member 312 such that blood flow exiting the one or more inflation ports 324 passes through the filter mesh prior to flowing through the one or more openings of the one or more porous regions, such as opening 350 of porous region 338. In some embodiments, the catheter 310 can include a filter mesh disposed in the interior of the catheter 310 adjacent the one or more inflation ports 324.

In other embodiments, the expandable member 312 can include one or more mesh or membrane regions extending along the area of the head vessels 342, 344, 346, instead of the discrete porous regions 338 formed by individual holes 350 made in the expandable member 312. In some embodiments, a single mesh or membrane region integrated into the expandable member 312 extends over the ostia of all of the head vessels 342, 344, 346.

The expandable member 312, and/or the one or more meshes, membranes, or other porous regions of the expandable member, can be made of any of a variety of biocompatible materials, including, but not limited to polyurethane, Pebax, Nylon, PET, PETE, PETN, PTFE, polypropylene, polyacrylamide, silicone, polymethylmethacrolate, Gore-Tex™, and/or ePTFE with a high internodal distance.

In some embodiments, the catheter 310 can include one or more porous members, such as one or more filter meshes, positioned adjacent the one or more perfusion ports 328. For example, the catheter 310 can include one or more filter meshes positioned on the exterior of the catheter 310 adjacent the one or more perfusion ports 328, or in the interior of the catheter 310 adjacent the one or more perfusion ports 328, as desired. In this manner, the one or more filter meshes can capture embolic material entrained in the blood flow exiting the one or more perfusion ports 328. In some embodiments, the catheter 310 can include a single filter mesh configured to filter blood exiting from the one or more inflation ports 324 and blood exiting from the one or more perfusion ports 328.

In some embodiments, the expandable member 312 and/or the catheter 310 can include a radiopaque marker 360, which can aid the surgeon in determining the location and/or orientation of the expandable member 312 during implantation.

In some embodiments, the material thickness of the expandable member 312 can be varied along its length and/or circumference. For example, in some embodiments, the material thickness of the proximal end portion 334 can be thicker or thinner than the material thickness of the distal end portion 336. When the distal end portion 336 is thinner, the distal end portion can be more compliant and can expand to a greater size, or more fully, than the proximal end portion 334 for a given pressure within the expandable member 312, as described above. In some embodiments, the expandable member 312 can comprise a balloon configured to elastically expand and contract, or to inflate and deflate inelastically, or both.

The aortic occlusion and perfusion device 300 can also include a flow control sheath 352, which can be coaxially disposed around the catheter 310 proximal to the expandable member 312. In some embodiments, the flow control sheath 352 can be axially movable along the catheter 310 such that the flow control sheath 352 can be selectively positioned over zero, one, or more of the one or more perfusion ports 328. When positioned over the one or more perfusion ports 328, the flow control sheath 352 can occlude or cover the one or more perfusion ports 328 such that blood is substantially prevented from flowing out of the first lumen 314 through the occluded perfusion port(s) 328. In this manner, the flow control sheath 352 can be used to control both the volume of blood exiting the catheter 310 through the perfusion ports 328, and the volume of blood entering the expandable member 312 through the inflation ports 324. As a result, the flow control sheath 352 can also be used to control the pressure inside the expandable member 312. For example, distal axial movement of the flow control sheath 352 relative to the catheter 310, as indicated by arrow 354, can cause the flow control sheath 352 to occlude an increased number of perfusion ports 328. This can cause an increased proportion of blood flow in the first lumen 314 to flow into the expandable member 312 relative to blood flow out of the perfusion ports 328, which can increase the pressure within the expandable member 312. Similarly, proximal axial movement of the flow control sheath 352 relative to the catheter 310, as indicated by arrow 356, can reduce the number of perfusion ports occluded by the flow control sheath 352 allowing greater blood flow out of the catheter 310 into the descending aorta 326. This can reduce the proportion of blood flow into the expandable member 312, which can lower the pressure in the expandable member 312.

In the embodiment shown, the catheter 310 can include a distal end portion 320 that extends distally from the distal end portion 336 of the expandable member 312 into the ascending aorta 304, as shown in FIG. 2. In the embodiment shown, the first lumen 314 can terminate at terminus 358 (indicated in phantom) located proximally of the distal end portion 320 of the catheter 310 such that the first lumen 314 is not in fluid communication with the distal end portion 320 of the catheter 310. In some embodiments, the terminus 358 can be, for example, an occluder or interior wall located at the distal end of the first lumen 314 that prevents blood flow beyond the terminus 358. The second and third lumens 316, 318 can be continuous through the distal end portion 320 of the catheter 310 such that they are in communication with the ascending aorta 322. In this manner, the second and third lumens 316, 318 can be used to, for example, deliver cardioplegia fluid, withdraw fluids such as blood (e.g., from the ascending aorta 322 and/or the left ventricle 308), insert and/or withdraw instruments, or relay signals (e.g., pressure, temperature, etc.) from any of various sensors that can be associated with the catheter 310.

The aortic occlusion and perfusion device 300 can be used in combination with the cardiac access system of FIG. 1, as described above. More specifically, the proximal end of the catheter 310 can be coupled to a cardiopulmonary bypass system such that the first lumen 314 is in fluid communication with an outlet of the cardiopulmonary bypass system. This can allow the cardiopulmonary bypass system to supply blood flow to both the one or more inflation ports 324 and the one or more perfusion ports 328 via the first lumen 314 of the catheter 310.

The device 300 can be advanced through a patient's vasculature with the expandable member 312 in a substantially collapsed or deflated state inside a delivery catheter. When the expandable member 312 reaches a desired location (e.g., the aortic arch 340), the device 300 can be advanced from the delivery catheter 102, and blood can be caused to enter the expandable member 312 through the first lumen 314 of the catheter 310, which can expand the expandable member 312 in the aortic arch 340. When the pressure inside the expandable member 312 reaches a predetermined pressure, the plurality of openings such as opening 350 of representative porous region 338 can open, allowing oxygenated blood to perfuse the head vessels 342, 344, 346. The pressure inside the expandable member 312, the volume of blood flowing into the head vessels 342, 344, 346 through the plurality of openings such as opening 350, and the volume of blood flowing into the descending aorta 326, can be controlled by covering and uncovering the perfusion ports 328 via axial movement of the flow control sheath 352 and/or by adjusting fluid pressure in the lumen 314 via the proximal controls. At the conclusion of the cardiac procedure, the heart can be restarted, the expandable member 312 can be deflated or otherwise allowed to collapse, and the device 300 can be withdrawn.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

What is claimed is:

1. An aortic occlusion and perfusion device, comprising:
an expandable member configured to expand within the aorta to secure the aortic occlusion and perfusion device within the aorta;
a catheter extending proximally from the expandable member and in fluid communication with the expandable member, the catheter defining openings along its length through which blood can pass with one or more of the openings being located proximal to the expandable member and one or more of the openings being located within the expandable member, the catheter defining a first lumen in fluid communication with the one or more openings located proximal to the expandable member and with the one or more openings located within the expandable member, the first lumen terminating at a terminus proximal to a distal end portion of the catheter, the catheter further defining a second lumen configured to be in communication with the ascending aorta; and a flow control sheath disposed around the catheter proximal to the expandable member such that axial movement of the flow control sheath relative to the catheter selectively occludes or uncovers the one or more openings located proximal to the expandable member.

2. The aortic occlusion and perfusion device of claim 1, wherein the expandable member includes one or more porous regions configured to be located adjacent the ostia of at least one of the brachiocephalic artery, the left common carotid artery, or the left subclavian artery.

3. The aortic occlusion and perfusion device of claim 2, wherein the one or more porous regions comprise a plurality of openings configured to open when the pressure inside the expandable member reaches a predetermined pressure.

4. The aortic occlusion and perfusion device of claim 2, wherein the one or more porous regions comprise a plurality of valves.

5. The aortic occlusion and perfusion device of claim 1, wherein:
the expandable member includes a proximal end portion and a distal end portion, and comprises an elastomeric material; and
a thickness of the elastomeric material at the proximal end portion is greater than a thickness of the elastomeric material at the distal end portion.

6. The aortic occlusion and perfusion device of claim 1, wherein the catheter is configured to be placed in fluid communication with the descending aorta via the one or more openings located proximal of the expandable member for perfusing blood to a lower portion of a patient's body.

7. The aortic occlusion and perfusion device of claim 6, wherein the flow control sheath is configured to control a flow of blood out of the catheter by selectively occluding the one or more openings located proximal to the expandable member.

8. The aortic occlusion and perfusion device of claim 1, wherein the expandable member is expandable by blood supplied to the expandable member through the catheter from an extracorporeal source.

9. An aortic occlusion and perfusion device, comprising:
an expandable member configured to expand within the aorta to secure the device within the aorta;
a catheter extending proximally from the expandable member and in fluid communication with the expandable member, the catheter defining a plurality of openings along its length through which blood can pass with one or more of the openings being located proximal to the expandable member and one or more of the openings being located within the expandable member; and
a flow control sheath disposed around the catheter proximal to the expandable member such that axial movement of the flow control sheath relative to the catheter selectively occludes or uncovers the one or more openings located proximal to the expandable member;
wherein the expandable member comprises three discrete porous regions spaced apart axially by non-porous regions, each of the porous regions being configured to be located adjacent the ostia of at least one of the brachiocephalic artery, the left common carotid artery, or the left subclavian artery.

10. The aortic occlusion and perfusion device of claim 9, wherein the expandable member is configured to be positioned in the aortic arch such that the three discrete porous regions are each positioned adjacent one of the brachiocephalic artery, the left common carotid artery, or the left subclavian artery.

11. A method of occluding blood flow through the aorta, comprising:
inserting an aortic occlusion and perfusion device including an expandable member into a patient's vasculature;
positioning the aortic occlusion and perfusion device in the aortic arch such that a distal end portion of the expandable member is located adjacent the ascending aorta and a proximal end portion of the expandable member is located adjacent the descending aorta;
expanding the expandable member with blood supplied by a catheter in fluid communication with the expandable member to secure the aortic occlusion and perfusion device within the aortic arch, the catheter extending proximally from the expandable member and defining openings along its length through which blood can pass, one or more of the openings being located proximal to the expandable member and one or more of the openings being located within the expandable member, the catheter defining a first lumen in fluid communication with the one or more openings located proximal to the expandable member and with the one or more openings located within the expandable member, the first lumen terminating at a terminus proximal to a distal end portion of the catheter, the catheter further defining a second lumen configured to be in communication with the ascending aorta;
controlling the pressure inside the expandable member by varying the flow rate of blood exiting the catheter through the one or more openings located proximal to the expandable member by axial movement of a flow control sheath disposed around the catheter proximal to the expandable member, the axial movement of the flow control sheath being relative to the catheter to selectively occlude or uncover the one or more openings located proximal to the expandable member.

12. The method of claim 11, wherein positioning the aortic occlusion device further comprises causing one or more porous regions of the expandable member to become positioned adjacent the ostium of at least one of the brachiocephalic artery, the left common carotid artery, or the left subclavian artery.

13. The method of claim 12, wherein the one or more porous regions comprise three discrete porous regions spaced apart axially by non-porous regions, and positioning the aortic occlusion device further comprises causing each of the three discrete porous regions to be positioned adjacent a respective one of the brachiocephalic artery, the left common carotid artery, and the left subclavian artery.

14. The method of claim 11, wherein expanding the expandable member further comprises expanding the expandable member until the pressure inside the expandable member reaches a predetermined pressure.

15. The method of claim 14, wherein expanding the expandable member to the predetermined pressure causes one or more openings associated with one or more porous regions to open.

16. The method of claim 11, wherein expanding the expandable member further comprises expanding the expandable member such that the distal end portion of the expandable member expands to a greater diameter than a diameter of the proximal end portion of the expandable member.

17. The method of claim 11, further comprising causing the expandable member to deflate and removing the deflated aortic occlusion and perfusion device from the body.

\* \* \* \* \*